United States Patent [19]

Smid et al.

[11] Patent Number: 5,490,950
[45] Date of Patent: Feb. 13, 1996

[54] LIQUID CONCENTRATED AQUEOUS SOLUTIONS OF SALTS OF ALKYL ETHER CARBOXYLIC ACID, AND A PROCESS FOR PREPARING SUCH SOLUTIONS

[75] Inventors: Jacob K. Smid, Doetinchem; Jacobus G. Verschuur, Gendringen, both of Netherlands

[73] Assignee: Chem-Y GmbH, Emmerich, Germany

[21] Appl. No.: 97,166

[22] Filed: Jul. 23, 1993

[30] Foreign Application Priority Data

Jul. 24, 1992 [NL] Netherlands ............ 9201339

[51] Int. Cl.$^6$ ............................................. C11D 1/72
[52] U.S. Cl. .............................................. 252/174.21
[58] Field of Search .................................. 252/174.21

[56] References Cited

U.S. PATENT DOCUMENTS 5,346,973   9/1994   Feustel et al. ............... 252/174.21 X

FOREIGN PATENT DOCUMENTS

| | | |
|---|---|---|
| 0019999 | 12/1980 | European Pat. Off. . |
| 0268992 | 6/1988 | European Pat. Off. . |
| 0344442 | 12/1989 | European Pat. Off. . |
| 0357561 | 3/1990 | European Pat. Off. . |
| 0384983 | 9/1990 | European Pat. Off. . |
| 9113140 | 9/1991 | WIPO . |
| 9208777 | 5/1992 | WIPO . |

OTHER PUBLICATIONS

Abstract J60071031 (Nippon Shokubai Kagaku)—Derwent Publications Ltd., London, GB, 1990.

*Primary Examiner*—Paul F. Shaver
*Attorney, Agent, or Firm*—Cooper & Dunham

[57] ABSTRACT

This invention relates to liquid concentrated aqueous solutions of salts of alkyl ether carboxylic acid derived from alkanols having at least 10 C atoms, which aqueous solution of the salts of alkyl ether carboxylic acid also contains ethoxylated or ethoxylated and carboxymethylated products or mixtures thereof, derived from polyhydric alcohols, the degree of ethoxylation of those products being at least 0.5. The invention also relates to processes for preparing such liquid aqueous solutions.

11 Claims, No Drawings

LIQUID CONCENTRATED AQUEOUS SOLUTIONS OF SALTS OF ALKYL ETHER CARBOXYLIC ACID, AND A PROCESS FOR PREPARING SUCH SOLUTIONS

This invention relates to liquid concentrated aqueous solutions of salts of alkyl ether carboxylic acid derived from alkanols having at least 10 C atoms, and to the preparation of such concentrated products.

It is known that salts of alkyl ether carboxylic acid may be used in a wide range of application, e.g. as dermatologically mild products having a cleaning effect in cosmetic uses and detergents, but also as additives in drilling and cutting oils, and as a dispersant. However, salts of alkyl ether carboxylic acid have the drawback that they are water soluble to a limited degree only, while retaining the liquid properties of the solution. The requirement generally imposed on these solutions is that they should be pumpable and homogeneous at room temperature. The solutions need not be completely clear; some turbidity does not detract from the homogeneity. At higher concentrations gelling generally occurs. This transfer from a liquid to a solid gelled product often does not proceed gradually, but rather very abruptly. The products are then not pumpable anymore and thus hard to process. In general, it may be stated that the products can hardly, if at all, be processed if the viscosity exceeds 80,000 mPa.s. Besides, the aqueous solutions should have a good cold stability up to 10°–15° C. For the purpose of the invention, cold stability is the temperature at which an undesirable change in the consistency of the product occurs, such as e.g. crystallization, phase separation or a drastic increase in the viscosity at a further temperature reduction. As a rule, the concentration of the aqueous solutions will therefore not exceed 25%, which has drawbacks with regard to transport and storage capacity. At such low concentrations it is generally also necessary to preserve the products from microbiological decay.

According to the state of the art, salts of alkyl ether carboxylic acid can only be provided as stable, at room temperature, concentrated liquid aqueous solutions if specific components are added to them. EP-A-0344442 discloses the use of mono- to trivalent $C_{1-6}$ alcohols as additives. Most of these alcohols, however, have an undesirably low flash point or spread an unpleasant odour. EP-A-0357561 indicates that at least two components selected from $C_{3-6}$ alkane diols and $C_{1-4}$ alkane glycol or alkane diglycol monoethers can be used as additives to obtain concentrated aqueous solutions of salts of alkyl ether carboxylic acid. A $C_{3-6}$ alcohol can be used to replace one of the said components or as an additional component. The degree of carboxymethylation of the salts of alkyl ether carboxylic acid in these products is high, e.g. 80%. The solutions are generally about 50%.

As already indicated above, the risk of gelling increases at increasing concentration. A substantial improvement of solubility, viscosity or cold stability cannot be obtained by using, instead of products having a high degree of carboxymethylation (i.e. 75–95%), corresponding products having a lower (e.g. 30–60%) degree of carboxymethylation. Thus, a likewise known product, Betader 1211 (of KaO Corporation), having a degree of carboxymethylation of about 60% can hardly be processed in solutions more concentrated than 22%.

For many uses, however, there is a need for easily obtainable, highly concentrated, e.g. at least 5%, pumpable and homogeneous solutions of salts of alkyl ether carboxylic acid that are still readily liquid at room temperature, but preferably also at 10°–15° C. It is true that an about 80% concentrated lauryl/myristyl 1OEO ether carboxylic acid salt having a low (about 40%) degree of carboxymethylation and good vicosity properties is known under the name of Sandopan LS24 Paste 115% (of Sandoz AG), but this could only be obtained by adding ethoxylated and/or carboxymethylated lower alcohols, such as hexanol. This product, however, has an undesirable sharp odour, which, in particular, is a serious impediment to cosmetic uses.

Finally, JP-A-60071031 discloses the use of an ethoxylated higher alcohol having an HLB of more than 11 as a viscosity controlling agent in solutions of salts of alkyl ether carboxylic acid having a concentration of more than 60 wt. %.

It is an object of the invention to provide homogeneous liquid concentrated aqueous solutions, pumpable at room temperature, of salts of alkyl ether carboxylic acid derived from alkanols having at least 10° C. atoms, which solutions can be rapidly diluted with water, and to readily prepare such concentrated solutions without the drawbacks of an unfavourable flash point and an unpleasant odour. A further requirement for such solutions is a favourable cold stability.

According to the invention, this object is achieved in that the aqueous solution of the salts of alkyl ether carboxylic acid derived from alkanols having at least 10 C atoms also contains ethoxylated or ethoxylated and carboxymethylated products or mixtures thereof derived from polyhydric alcohols, the degree of ethoxylation of those products being at least 0.5.

For the purpose of this invention, the degree of ethoxylation is the average number of moles of ethylene oxide added per hydroxyl group of the starting compound (in the unethoxylated form thereof).

Hereinbelow the salts of alkyl ether carboxylic acid will also be referred to as "products A", while of the other products present within the scope of this invention the ethoxylated products will also be referred to as "products B" and the ethoxylated and carboxymethylated products will also be referred to as "products C".

Products A used within the scope of the invention are known per se. These are compounds having a general formula

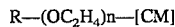

$$R-(OC_2H_4)n-[CM]$$

in which R represents a branched or straight alkyl group having at most 30 C atoms and a longest chain of 10–22 C atoms, n indicates the degree of ethoxylation ("EO degree") having a value of 0.5–20, in particular 2.1–16, more in particular 6–12, [CM] represents the carboxymethylation fraction and therefore corresponds to $(OCH_2COOM)_q$, which means that $OH_{(1-q)}$ is also present, M representing an alkali metal ion or ammonium ion, in particular a sodium ion, and q being maximally 0.95, and in particular a value ranging from 0.3 to 0.75, more in particular from 0.4 to 0.6. By means of variation of n, q and M the product properties can be further influenced. A skilled worker can readily determine this. Variation of n and q occurs in the ethoxylation and carboxymethylation reactions; variation of M may occur by first purifying the resulting carboxymethylation product by treating it at high temperature with a mineral acid and separating the resulting free carboxylic acid, and then neutralizing it with a base derived from M.

Products B have been derived from polyhydric alcohols or mixtures thereof by means of ethoxylation and have a degree of ethoxylation of at least 0.5, in particular more than 2.1. In this connection, diethylene glycol, polyethylene glycols (PEG's) and other already ethoxylated polyhydric alcohols are also regarded as polyhydric alcohols. Examples of such products B are PEG300, PEG1500, glycerin having an EO degree of e.g. 2; 4; 4.5 or 10, trimethylolpropane having an EO degree of e.g. 10, and by further ethoxylation of secondary products obtained therefrom. Products derived from glycerin are preferred in connection with their dermatological properties.

Products C are obtained by ethoxylation and subsequent partial carboxymethylation starting from polyhydric alcohols or mixtures thereof and have a degree of ethoxylation of at least 0.5 and are further determined by the degree of carboxymethylation (CM degree). The ethoxylation and carboxymethylation reactions for the preparation of products C can be carried out both simultaneously with the corresponding preparation of products A (and also in the same ethoxylation or carboxymethylation reactor), or separately from the preparation of products A and with optionally other amounts of the reactants. In the latter case, another CM degree can be obtained for products C than for products A. The CM degree of products C will generally not exceed 0.95 per hydroxyl group and in particular range from 0.3 to 0.75, more in particular from 0.4 to 0.6.

It is further observed here that both for products B and for products C the EO degree can be influenced separately by selecting the starting material used as polyhydric alcohol. If, for this purpose, already ethoxylated compounds are used, such as PEG's, the EO degree of products A departs from that of products B and/or C, even in the variant of embodiment first mentioned above (common reaction). Then, however, for products B and/or C there is an "additional EO degree", corresponding to the EO degree of products A.

Excellent results according to the invention are obtained if products C are prepared simultaneously with products A, so that, as far as the CM and (additional) EO degree is concerned, products C are therefore comparable to the salts of alkyl ether carboxylic acid (products A). For the purpose of this invention, a comparable CM and (additional) EO degree is therefore the CM and (additional) EO degree of products C, obtained if the polyhydric alcohols used therefor are ethoxylated and carboxymethylated simultaneously with the starting material used for the salts of alkyl ether carboxylic acid. The term "additional EO degree" is to be used if there are already ethoxylated starting compounds for product C. Hereinbelow reference will only be made to the EO degree, but, accordingly, this term comprises the additional EO degree.

In another embodiment of the invention, excellent results are also obtained by mixing products A with separately prepared products B and/or C, in which the EO degree, or the EO and CM degree, is comparable to that of products A.

In a last embodiment, suitable concentrated aqueous solutions are also obtained according to the invention by mixing products A with separately prepared products B and/or C, in which the EO degree, or the EO and CM degree, departs from that of products A.

The EO degree, or the EO and CM degree, of products B and/or C does not prove very critical for the results obtained. By varying the EO degree, or the EO and CM degree, of compounds B or C, a skilled worker can readily prepare suitable compositions according to the invention.

The content of products B and/or C in the concentrated solutions according to the invention may vary within broad limits, but should be adjusted within limits that can be determined by using the following rules of thumb which, among other things, relate the amount of products B and/or C to the total amount of solids: products B and/or C must, expressed in weight percents, be present in the solution in an amount of at least 1%, in particular 2–25% relative to the total amount of solids of A plus B and/or C. An amount of 5–15% is often sufficient, in particular when using products C in the solution. If the amounts of products B and/or C are below the above lower limit, no effect is found. If the amounts are above the indicated upper limit, no additional advantage is obtained anymore.

The amount of water to be added to the mixture of products A and B and/or C in order to obtain a homogeneous liquid aqueous solution, pumpable at room temperature, is such that, as a rule, at most 55% (weight relative to the weight of the solution), and preferably at most 30%, will be present. Of course, a larger amount of water may also be added, but then the advantages of the solution being concentrated will be lost. Also, more diluted solutions require the use of preservatives against microbiological decay. Subject to the desired cold stability of the solution, a skilled worker can readily determine the minimally required amounts of water and products B and/or C. An important advantage of the present concentrated aqueous solutions is that their rate of solution is substantially higher than that of corresponding solutions, which, however, do not contain the products derived from polyhydric alcohols. This advantage is important for the adjustment of the desired concentration and in the later use of the concentrated solutions.

The invention will now be further explained by the following examples, also in comparison with the comparative examples likewise described below, but without being limited thereto:

EXPERIMENTAL PART:

A. Preparation of raw materials and/or additives for use in the following experiments.

A. 1. Alkyl-10 EO-nonionic As an example of an ethoxylated alkanol derivative derived from an alkanol having at least 10 C atoms, an ethoxylated secondary product was prepared from Lorol 1216 (a commercial product of Henkel having a rough composition consisting of about 65% lauryl alcohol, about 25% myristyl alcohol and about 10% cetyl alcohol) by condensating 1751 g Lorol 1216 (8.93 equivalents) in a stainless steel autoclave at 175° C. in the presence of sodium hydroxide (NaOH) prills as catalyst with 3932 g ethylene oxide (89.4 equivalents). The resulting reaction product, a 10 EO-nonionic, in total 5683 g, will hereinbelow be referred to as [A1], for simplicity's sake.

A. 2. Alkyl-10 EO-carboxylic acid salt

An example of a separately prepared salt of alkyl ether carboxylic acid was obtained by partial carboxymethylation of [A1]. This was done by stirring 800 g of [A1] (1.28 equivalents) in a beaker at about 70° C. while adding, in four portions for 2 hours, in total 81.8 g sodium monochloroacetate (SMCA) (0.70 equivalents) and 28.4 g NaOH prills (0.71 equivalents) and subjecting the same to a subsequent reaction for 2 hours at 70° C. At the end of the reaction, 902 g of a product having a degree of carboxymethylation of 46% were obtained as a white paste, which will hereinbelow be referred to as [A2], also for simplicity's sake.

A.3. Washed alkyl-10 EO-carboxylic acid salt From a relatively crude alkyl ether carboxylic acid salt, as e.g. obtained above in A. 2., there can also be obtained a purer product by first converting the crude product with hydrochloric acid into the free acid. This procedure, also referred to as washing, may be repeated a few times, if need be, for further purification and must be followed if the cation of the original salt is to be replaced by another cation. By way of example, 300 g of [A2] were heated to 90° C. and added, in a glass reaction vessel while stirring, to 112 g of an aqueous solution of hydrochloric acid, likewise maintained at 90° C.

After 15 minutes stirring the stirrer was stopped, and—after unmixing—the water layer was removed. The remaining colourless product containing the free alkyl-10 EO-carboxylic acid was also liquid at room temperature. This procedure was repeated a few times for fresh portions of crude [A2]. After analysis, the total product collected was found to contain 7.9 wt. % water and 0.60 meq/g of anionactive substance (potentiometrically determined).

Subsequently, 48.5 g 50% caustic soda was gradually added to 967 g of this product at room temperature, the temperature remaining below 50° C. There were obtained 1013 g of a clear liquid product, which, however, turned white and solid after one night standing at room temperature. Analysis of this product, hereinafter referred to as [A3], gave the following results:

water content: 11 wt.% chloride content (potentiometric): 0.16 meq/g.

A part of product [A3] was diluted with water, at 40° C., to obtain a concentrate having a water content of 25 wt. %, which, when cooled to room temperature, gave a gel.

Glycerin-10 EO

Analogously to the manner described above for the preparation of [A1], but with the proviso that, in connection with the degree of filling of the autoclave, the reaction had to be carried out in two steps, there was produced an ethoxylated glycerin derivative to be used as an additive within the scope of the invention. In a first step, 344 g glycerin (1,2,3-propanetriol; 11.22 equivalents) were introduced into the autoclave with 998 g ethylene oxide (22.68 equivalents). The reaction product obtained therefrom, 1342 g, has an average number of oxyethylene groups of 2.02 per hydroxyl group in glycerin.

Subsequently, of this product obtained 380 g (3.18 equivalents) were analogously introduced into the same autoclave with 1081 g ethylene oxide (24.57 equivalents). The product resulting after the reaction, solid at room temperature, weighed 1461 g. Per original mole of glycerin, 29.3 moles of ethylene oxide are incorporated in this product, which, per hydroxyl group, corresponds to nearly 10 oxyethylene units. For simplicity's sake, this product will hereinbelow be referred to as [A4].

A.5. Glycerin-10 EO-carboxylic acid salt

Carboxymethylation of [A4] was carried out analogously to the process defined under A.2. to obtain a—separately prepared—carboxymethylated ethoxylated glycerin derivative in salt form. To that end, 400 g of [A4] (0.87 equivalents), 54.4 g SMCA (0.47 equivalents) and 18.9 g NaOH (0.47 equivalents) were reacted as defined in A.2. There were obtained 468 g of a slightly yellow paste, which, for simplicity's sake, will hereinbelow be referred to as [A5].

A.6. Alkyl10 EO-carboxylic acid salt having a high degree of carboxymethylation

Analogously to the manner described under A.2. in combination with A.3. for the preparation of a washed and neutralized product having an about 46% degree of carboxymethylation, a corresponding product having an about 85% degree of carboxymethylation was also prepared, but starting from another molar ratio of reactants.

There was started from 630 g of [A1], 175 g SMCA and 60 g NaOH. The reaction resulted in 853 g of a pasty product which solidified at room temperature. This was acidified and neutralized again, in conformity with the process defined under A.3. This resulted in a product white and solid at room temperature, which, for simplicity's sake, will hereinafter be referred to as [A6].

A. 7. Alkyl-4,5 EO -nonionic

Analogously to the manner described under A.1., starting from Lorol Spezial (about 73% lauryl alcohol, about 25% myristyl alcohol, about 2% decyl alcohol, and cetyl alcohol), an ethoxylate was prepared with an average of 4.5 moles of ethylene oxide per mole of alkanol. For simplicity's sake, this product will hereinafter be referred to as [A7].

A. 8. Glycerin-4:5 EO

Analogously to the manner described under A.4., glycerin-4.5 EO was prepared (an average of 4.5 EO groups per OH group). For simplicity's sake, this product will hereinafter be referred to as [A8].

B. Examples and Comparative Examples

EXAMPLE 1

610 g of the paste of salt of alkyl ether carboxylic acid [A2] and 67.8 g of the ethoxylated polyhydric alcohol [A4] were heated to about 50° C. in a 2 liter beaker and stirred to obtain a homogeneous product. The water content of this mixture was determined to be 0.7 wt. %. Subsequently, 220 g water of about 60° C. were added, so that a total water content of 25 wt. % was obtained. The clear concentrated solution thus obtained was also at room temperature liquid and pumpable, even after storage for 12 months at 18°–20° C.

At this solution the following determinations were carried out for characterization:

water content: 25 wt.% chloride content (potentiometric): 0.56 meq/g anionactive substance: 0.44 meq/g pH (diluted to 10% aqueous solution, and at 20° C.): 7.2 viscosity (20° C): 1000 mPa.s

For comparison: without the presence of [A4] a clear and pumpable product liquid at 20° C., having a viscosity of 40 mPa.s, could be obtained from [A2] only by diluting to a solution having a water content of 75 wt. %. When diluting [A2], without the presence of an additive according to the invention, to 75% or 50% solids content, there were always obtained products which spontaneously formed a gel. The resulting gels were found incapable of being broken by adding additional amounts of salt.

EXAMPLE 2

Analogously to the manner described in Example 1, but now in a 0.5 liter beaker, 72 g of the paste of [A2] and 8 g of the paste of [A5] were mixed and heated to about 50° C., after which the water content was adjusted to 25 wt. %.

The clear concentrated solution thus obtained was also at room temperature liquid and pumpable, even after storage for 12 hours at 18°–20° C.

Various determinations gave the following results:

water content: 25 wt. % chloride content (potentiometric): 0.65 meq/g anionactive substance: 0.48 meq/g pH (10% aq. ): 7.2

| viscosity | (20° C.): | 750 mPa.s |
|---|---|---|
|  | (15° C.): | 2600 mPa.s. |

EXAMPLE 3

In the manner as described under A.2. a mixture of 400 g of [A1] and 44.4 g of [A4] was carboxymethylated with 42.9 g SMCA and 14.9 g NaOH. These amounts correspond, expressed in equivalents, to respectively 0.64, 0.096, 0.37 and 0.37. The reaction gave a white paste which was adjusted with water of 60° C. to 75 wt. % solids. The clear concentrated solution thus obtained was also at room temperature liquid and pumpable, even after storage for 12 months at 18°–20° C.

Various determinations gave the following results:

water content: 25 wt. % chloride content (potentiometric): 0.62 meq/g anionactive substance: 0.46 meq/g pH (10% aq.): 6.2 viscosity (20° C.): 750 mPa.s

EXAMPLE 4

1562 g of the alkanol mixture Lorol 1216 (as also used above in A.1. ) were mixed with 36.3 g glycerin. This mixture was then ethoxylated in the manner described under A.1.) with 3980 g ethylene oxide in a stainless steel autoclave. Thus, 5580 g of a "mixed ethoxylate" product were obtained. The reaction was carried out a second time under the same conditions and with the same amounts of reactants to obtain a larger amount of "mixed ethoxylate" product. Of the total product thus obtained, 8584 g (or 14.08 equivalents) were carboxymethylated with 909 g SMCA (7.8 equivalents) and 315 g NaOH (7.88 eqivalents) in a 30 l reactor, analogously to the manner described in A.2. The resulting product was diluted with water of 60° C. to 75 wt. % solids content. The clear concentrated solution thus obtained was also at room temperature liquid and pumpable, even after storage for 12 months at 18°–20° C.

Various determinations gave the following results:

water content: 25 wt. % chloride content (potentiometric): 0.73 meq/g anionactive substance: 0.50 meq/g pH (10% aq.): 6.2

| viscosity | (20° C.): | 750 mPa.s |
|---|---|---|
| | (15° C.): | 1250 mPa.s |
| | (10° C.): | 2100 mPa.s |

(10° C.): 2100 mPa.s

Rate of solution from 75 wt. % solids to 22 wt. % solids (at room temperature): 2¼ minutes.

EXAMPLE 5

50 g of the white, solid [A3] were heated to about 40° C. to liquefy the product and mixed with 5.0 g of [A4]. The water content was then adjusted to 25 wt. %, which resulted in a colourless liquid, also at low temperatures liquid and pumpable.

Various determinations gave the following results:

water content: 25 wt. % chloride content (potentiometric): 0.12 meq/g anionactive substance: 0.43 meq/g pH (10% aq.): 7.0

| viscosity | (20° C.): | 750 mPa.s |
|---|---|---|
| | (15° C.): | 1250 mPa.s |
| | (10° C.): | 2000 mPa.s. |

EXAMPLE 6

Example 5 was repeated, but now using 5.0 g of [A5] instead of [A4]. This also resulted in a colourless liquid, liquid and pumpable at room temperature. Various determinations gave the following results:

water content: 25 wt. % chloride content (potentiometric): 0.20 meq/g anionactive substance: 0.47 meq/g pH (10% aq.): 7.0

| viscosity | (20° C.): | 750 mPa.s |
|---|---|---|
| | (15° C.): | 1250 mPa.s |
| | (10° C.): | 2000 mPa.s. |

EXAMPLE 7

285 g of the white and solid [A6] were heated to about 60° C. to liquefy the product and mixed with 15 g of [A4], after which the mixture was diluted with water of 60° C. to obtain a solids content of 80 wt. %. This product, although slightly turbid at 20° C., is readily liquid and pumpable at that temperature.

For comparison, it is stated that [A6], if diluted with water to 80 wt. %, 75 wt. % and 50 wt. % solids, gives a thick gel in all cases if no additive according to the invention is added.

EXAMPLE 8

The invention may further be explained by the following schematic survey of additional experiments with other additives or other compositions tested by applicants.

a) mixtures of [A2] and amounts, listed in the table, of separately obtained products B were prepared analogously to the process of Example 1 and diluted with water to obtain the solids contents listed in Table 1 below. In all cases, concentrated, homogeneous solutions of the salt of alkyl ether carboxylic acid [A2], liquid at 20° C. and readily pumpable, were obtained:

TABLE 1

| product B content | wt. % B relative to [A2] + B | solids (%) |
|---|---|---|
| 8.1.1. PEG.600 | 20 | 90 |
| 8.1.2. PEG.600 | 20 | 85 |
| 8.1.3. PEG.600 | 20 | 80 |
| 8.1.4. PEG.600 | 20 | 75 |
| 8.2.1. glycerin 2,4 EO | 10 | 80 |
| 8.2.2. glycerin 2,4 EO | 10 | 75 | b) mixtures of [A2] and separately obtained products C were prepared analogously to the process of Example 2 and diluted with water to obtain the solids contents listed in Table 2 below. In all cases, concentrated, homogeneous solutions of the salt of alkyl ether carboxylic acid [A2], liquid at 20° C. and readily pumpable, were obtained:

TABLE 2

| product C content | wt. % C relative to [A2] + C | solids (%) |
|---|---|---|
| 8.3.1. PEG.600 CZZ | 10 | 75 |
| 8.3.2. PEG.600 CZZ | 15 | 75 |
| 8.3.3. PEG.600 CZZ | 20 | 85 |

TABLE 2-continued

| product C content | wt. % C relative to [A2] + C | solids (%) |
|---|---|---|
| 8.3.4. PEG.600 CZZ | 20 | 75 | b) Analogously to the manner described in Example 3 mixtures of [A1] and amounts, listed in Table 3, of products B were (together) carboxymethylated to obtain a degree of carboxymethylation of about 45% and then diluted with water to obtain the solids contents listed in Table 3. In all cases, concentrated, homogeneous solutions of the salt of alkyl ether carboxylic acid [A2], liquid at 20° C. and readily pumpable, were obtained:

TABLE 3

| | mixture to be carboxymethylated | |
|---|---|---|
| product B content | wt. % B relative to [A1] + B | solids (%) |
| 8.4.1. PEG. 600 | 10 | 75 |
| 8.4.2. PEG.1500 | 10 | 75 |
| 8.5.1. glycerin 2,4 EO | 5 | 80 |
| 8.5.2. glycerin 2,4 EO | 5 | 75 |
| 8.6.1. [A4] | 5 | 75 |
| 8.6.2. [A4] | 10 | 75 |
| 8.6.3. [A4] | 15 | 80 |
| 8.6.4. [A4] | 15 | 75 |
| 8.7.1. trimethylol-propane 10 EO | 10 | 80 |
| 8.7.2. trimethylol-propane 10 EO | 10 | 75 | d) Analogously to Example 4, starting from glycerin and Lorol 1216, combined ethoxylation and carboxymethylation reactions were carried out, in which the amount of glycerin relative to Lorol 1216 was selected so that up to 10 EO 10% [A4] and 90% [A1] were present in the mixture after the ethoxylation.

After carboxymethylation to a degree of carboxymethylation of about 45% there was diluted with water to obtain a solids content of respectively 75 and 50%. In all cases, concentrated, homogeneous solutions of the salt of alkyl ether carboxylic acid [A2], liquid at 20° C. and readily pumpable, were obtained:

NB: With respect to the starting materials used in Example 8 it is stated that:

PEG 600 is a commercially available polyethylene glycol having an average molecular weight of 600 glycerin 2,4 EO is a glycerin derivative in which 2,4 equivalents of ethylene oxide are incorporated per original hydroxyl group of glycerin PEG 600.CZZ is a carboxylic acid salt derived from PEG 600, obtained by carboxymethylation, having a degree of about 45%

PEG 1500 is analogous to PEG 600, but now having an average molecular weight of 1500 trimethylolpropane 10 EO, as far as the method of preparation is concerned, is comparable to A.4, but starting from trimethylolpropane ([2-ethyl-2-hydroxymethyl]-1,3 -propanediol).

EXAMPLE 9

Analogously to the manner described under A.2., a mixture of 425 g A7 and 75 g A8 was carboxymethylated with 89.4 g SMCA and 30.7 g NaOH. These amounts correspond, expressed in equivalents, to respectively 1.06; 0.33; 0.77; and 0.77.

The reaction gave a white paste, which, after neutralization with hydrochloric acid, was adjusted with water to 70 wt. % solids.

Various determinations gave the following results:

water content: 30 wt. % pH (10% aq.): 7.1 anionactive substance: 0.60 meq/g chloride content (potentiometric): 0.60 meq/g viscosity (20° C.): 13000 mPa.s (thixotropic)

rate of solution from 70 wt. % solids to 22 wt. % solids (at room temperature): 2½ minutes.

EXAMPLE 10 (Comparative Example)

Analogously to the manner described under A.2., 502 g A7 was carboxymethylated with 80.6 g SMCA and 27.7 g NaOH.

These amounts correspond, expressed in equivalents, to respectively 1.26; 0.69; and 0.69.

The reaction gave a white paste, which, after neutralization with hydrochloric acid, was adjusted with water to 70 wt. % solids.

Various determinations gave the following results:

water content: 30 wt. % pH (10% aq.): 7.2 anionactive substance: 0.7 6 meq/g chloride content (potentiometric): 0.62 meq/g viscosity (20° C.): 93000 mPa.s rate of solution from 70 wt. % solids to 22 wt. % solids (at room temperature): 1¾ hours.

We claim:

1. Liquid concentrated aqueous solutions of salts of alkyl ether carboxylic acid derived from alkanols having at least 10 C atoms, characterized in that the aqueous solution of the salts of alkyl ether carboxylic acid also contains ethoxylated or ethoxylated and carboxymethylated products or mixtures thereof, derived from polyhydric alcohols, the degree of ethoxylation of said products being at least 0.5.

2. Liquid concentrated aqueous solutions according to claim 1, in which the degree of ethoxylation of the products is at least 2.1.

3. Liquid concentrated aqueous solutions according to claim 1 in which the polyhydric alcohol is glycerin.

4. Liquid concentrated aqueous solutions according to claim 1, in which the degree of carboxymethylation of the products derived from the polyhydric alcohol is at most 0.95.

5. Liquid concentrated aqueous solutions according to claim 1, in which the carboxymethylated product derived from the polyhydric alcohol is present as sodium salt.

6. Liquid concentrated aqueous solutions according to claim 1, in which the employed salts of alkyl ether carboxylic acid are compounds having a general formula

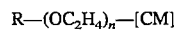

R—(OC$_2$H$_4$)$_n$—[CM]

in which R represents a branched or straight alkyl group having at most 30 C atoms and a longest chain of 10–22 C atoms, n indicates the degree of ethoxylation ("EO degree") having a value of 0.5–20, [CM] corresponds to the total of (OCH$_2$COOM)$_q$ and OH$_{(1-q)}$, M representing an alkali metal ion or ammonium ion, in particular a sodium ion, and q being maximally 0.95.

7. Liquid concentrated aqueous solutions according to claim 6, in which the degree of ethoxylation and/or the degree of carboxymethylation of the ethoxylated and/or carboxymethylated products derived from the polyhydric alcohol correspond to those of the salts of alkyl ether carboxylic acid.

8. Liquid concentrated aqueous solutions according to claim 6, in which the carboxymethylated products are present as sodium salt.

9. Liquid concentrated aqueous solutions according to claim 6, in which the amount of the ethoxylated or ethoxylated and carboxymethylated products derived from the polyhydric alcohol is at least 1 wt. % relative to the dry weight of the total of these products and the salts of alkyl ether carboxylic acid.

10. Liquid concentrated aqueous solutions according to claim 6, in which the aqueous solution contains at most 55 wt. % water relative to the total weight of the solution.

11. A process for preparing liquid concentrated aqueous solutions of salts of alkyl ether carboxylic acid derived from alkanols having at least 10 C atoms, characterized in that by successively ethoxylating and carboxymethylating a mixture of an alkanol and one or more polyhydric alcohols a salt of alkyl ether carboxylic acid is prepared in which the degree of ethoxylation is at least 0.5 and the resulting mixture is diluted so as to form a pumpable, liquid solution having a solids content of at least 45 wt. %.

* * * * *